(12) United States Patent
Fox et al.

(10) Patent No.: US 10,080,529 B2
(45) Date of Patent: Sep. 25, 2018

(54) SYSTEM FOR MONITORING PHYSIOLOGICAL CHARACTERISTICS

(71) Applicant: MEDTRONIC MINIMED, INC., Northridge, CA (US)

(72) Inventors: James Kelly Fox, Valencia, CA (US); Garry M. Steil, Pasadena, CA (US); Kerstin Rebrin, Pasadena, CA (US); Mark C. Estes, Simi Valley, CA (US); Frank Saidara, Los Angeles, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 286 days.

(21) Appl. No.: 14/599,010

(22) Filed: Jan. 16, 2015

(65) Prior Publication Data

US 2015/0190100 A1 Jul. 9, 2015

Related U.S. Application Data

(60) Continuation-in-part of application No. 11/807,786, filed on May 30, 2007, now Pat. No. 8,961,416,
(Continued)

(51) Int. Cl.
*A61B 5/1486* (2006.01)
*G16H 40/63* (2018.01)
(Continued)

(52) U.S. Cl.
CPC ............ *A61B 5/746* (2013.01); *A61B 5/1495* (2013.01); *A61B 5/14532* (2013.01);
(Continued)

(58) Field of Classification Search
CPC .... A61B 2560/0223; A61B 2560/0252; A61B 2560/045; A61B 5/0002; A61B 5/14532;
(Continued)

(56) References Cited

U.S. PATENT DOCUMENTS 3,701,345 A 10/1972 Heilman et al.
4,276,888 A 7/1981 Smith et al.
(Continued)

FOREIGN PATENT DOCUMENTS

CA 2550855 C 7/2005
DE 10108862 A1 2/2001
(Continued)

*Primary Examiner* — Navin Natnithithadha
(74) *Attorney, Agent, or Firm* — Medtronic MiniMed, Inc.

(57) ABSTRACT

Apparatuses and methods for medical monitoring physiological characteristics values such as blood glucose levels for the treatment of diabetes, are presented. The apparatuses and methods provide dynamic glucose monitoring functions that perform predictive analysis to anticipate harmful conditions, such as glucose crash and hyperglycemic incidents for a patient. The dynamic functions can also be used to maximize athletic performance and warn of inadequate nocturnal basal rate. Other aspects include advanced alarm and reminder functions, as well as advanced data presentation tools to further facilitate convenient and efficient management of various physiological conditions.

13 Claims, 10 Drawing Sheets

Related U.S. Application Data which is a division of application No. 10/750,080, filed on Dec. 31, 2003, which is a continuation-in-part of application No. 10/034,139, filed on Dec. 27, 2001, now Pat. No. 7,022,072.

(51) Int. Cl.

| | | |
|---|---|---|
| *G16H 15/00* | (2018.01) | |
| *A61B 5/1468* | (2006.01) | |
| *A61B 5/1495* | (2006.01) | |
| *A61B 5/00* | (2006.01) | |
| *A61B 5/145* | (2006.01) | |
| *G06F 19/00* | (2018.01) | |

(52) U.S. Cl.
CPC ...... *G06F 19/3418* (2013.01); *G06F 19/3456* (2013.01); *G16H 15/00* (2018.01); *G16H 40/63* (2018.01); *A61B 5/0002* (2013.01); *A61B 5/1468* (2013.01); *A61B 5/1486* (2013.01); *A61B 5/7275* (2013.01); *A61B 2560/0223* (2013.01); *A61B 2560/0252* (2013.01); *A61B 2560/045* (2013.01)

(58) Field of Classification Search
CPC ... A61B 5/1468; A61B 5/1486; A61B 5/7275; A61B 5/1495; A61B 5/746; G06F 19/3406; G06F 19/3487; G06F 19/3418; G06F 19/3456
USPC .......................................... 600/309, 345–366
See application file for complete search history.

(56) References Cited

U.S. PATENT DOCUMENTS

| | | | |
|---|---|---|---|
| 4,385,272 A | 5/1983 | Whitehead | |
| 4,498,479 A | 2/1985 | Martio et al. | |
| 4,510,346 A | 4/1985 | Bursh, Jr. et al. | |
| 4,562,751 A | 1/1986 | Nason et al. | |
| 4,573,994 A | 3/1986 | Fischell et al. | |
| 4,619,646 A | 10/1986 | Hernandez et al. | |
| 4,676,568 A | 6/1987 | Nault et al. | |
| 4,678,408 A | 7/1987 | Nason et al. | |
| 4,685,903 A | 8/1987 | Cable et al. | |
| 4,731,726 A | 3/1988 | Allen, III | |
| 4,747,824 A | 5/1988 | Spinello | |
| 4,755,173 A | 7/1988 | Konopka et al. | |
| 4,760,730 A | 8/1988 | Frank et al. | |
| 4,857,857 A | 8/1989 | Valenti et al. | |
| 5,080,653 A | 1/1992 | Voss et al. | |
| 5,097,122 A | 3/1992 | Colman et al. | |
| 5,124,661 A | 6/1992 | Zelin et al. | |
| 5,219,099 A | 6/1993 | Spence et al. | |
| 5,233,986 A | 8/1993 | Robson | |
| 5,299,571 A | 4/1994 | Mastrototaro | |
| 5,376,070 A | 12/1994 | Purvis et al. | |
| 5,390,671 A | 2/1995 | Lord et al. | |
| 5,391,250 A | 2/1995 | Cheney, II et al. | |
| 5,414,213 A | 5/1995 | Hillburn | |
| 5,482,473 A | 1/1996 | Lord et al. | |
| 5,485,408 A | 1/1996 | Blomquist | |
| 5,497,772 A * | 3/1996 | Schulman ........... A61B 5/14865 | |
| | | | 204/403.09 |
| 5,522,803 A | 6/1996 | Teissen-Simony | |
| 5,523,534 A | 6/1996 | Meister et al. | |
| 5,557,210 A | 9/1996 | Cappa et al. | |
| 5,569,186 A | 10/1996 | Lord et al. | |
| 5,586,553 A | 12/1996 | Halili et al. | |
| 5,651,367 A | 7/1997 | Schloemer et al. | |
| 5,660,163 A | 8/1997 | Schulman et al. | |
| 5,665,065 A | 9/1997 | Colman et al. | |
| 5,683,270 A | 11/1997 | Warislohner | |
| 5,746,697 A * | 5/1998 | Swedlow ........... A61B 5/14551 | |
| | | | 600/323 |
| 5,781,024 A | 7/1998 | Blomberg et al. | |
| 5,791,344 A * | 8/1998 | Schulman ........... A61B 5/14865 | |
| | | | 204/403.11 |
| 5,792,068 A | 8/1998 | Bowman et al. | |
| 5,800,420 A | 9/1998 | Gross et al. | |
| 5,807,375 A | 9/1998 | Gross et al. | |
| 5,822,715 A | 10/1998 | Worthington et al. | |
| 5,824,959 A | 10/1998 | Mista et al. | |
| 5,834,699 A | 11/1998 | Buck et al. | |
| 5,865,736 A | 2/1999 | Baker, Jr. et al. | |
| 5,913,310 A | 6/1999 | Brown | |
| 5,924,979 A * | 7/1999 | Swedlow ........... A61B 5/14551 | |
| | | | 600/300 |
| 5,925,021 A | 7/1999 | Castellano et al. | |
| 5,954,643 A | 9/1999 | Van Antwerp et al. | |
| 6,017,328 A | 1/2000 | Fischell et al. | |
| 6,030,346 A | 2/2000 | Buck et al. | |
| 6,068,594 A | 5/2000 | Schloemer et al. | |
| 6,113,537 A | 9/2000 | Castano | |
| 6,117,083 A | 9/2000 | Buck et al. | |
| 6,175,752 B1 | 1/2001 | Say et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,272,364 B1 | 8/2001 | Kurnik | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,551,276 B1 | 4/2003 | Mann et al. | |
| 6,558,351 B1 | 5/2003 | Steil et al. | |
| 6,572,542 B1 | 6/2003 | Houben et al. | |
| 6,591,876 B2 | 7/2003 | Safabash | |
| 6,641,533 B2 | 11/2003 | Causey, III et al. | |
| 6,725,074 B1 | 4/2004 | Kastle | |
| 6,736,797 B1 | 5/2004 | Larsen et al. | |
| 6,749,587 B2 | 6/2004 | Flaherty | |
| 6,754,516 B2 | 6/2004 | Mannheimer | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,862,466 B2 * | 3/2005 | Ackerman ........... A61B 5/14532 | |
| | | | 600/347 |
| 6,893,396 B2 | 5/2005 | Schulze et al. | |
| 7,003,336 B2 | 2/2006 | Holker et al. | |
| 7,011,630 B2 * | 3/2006 | Desai ................. A61B 5/14532 | |
| | | | 204/403.01 |
| 7,022,072 B2 | 4/2006 | Fox et al. | |
| 7,029,444 B2 | 4/2006 | Shin et al. | |
| 7,048,687 B1 | 5/2006 | Reuss et al. | |
| 7,052,472 B1 | 5/2006 | Miller et al. | |
| 7,066,909 B1 | 6/2006 | Peter et al. | |
| 7,123,950 B2 | 10/2006 | Mannheimer | |
| 7,137,964 B2 | 11/2006 | Flaherty | |
| 7,228,163 B2 * | 6/2007 | Ackerman ........... A61B 5/14532 | |
| | | | 600/345 |
| 7,278,983 B2 | 10/2007 | Ireland et al. | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,654,948 B2 | 2/2010 | Kaplan et al. | |
| 7,699,775 B2 * | 4/2010 | Desai ................. A61B 5/14532 | |
| | | | 600/309 |
| 7,699,807 B2 | 4/2010 | Faust et al. | |
| 7,727,148 B2 | 6/2010 | Talbot et al. | |
| 7,766,830 B2 * | 8/2010 | Fox ..................... A61B 5/14532 | |
| | | | 600/347 |
| 7,774,145 B2 * | 8/2010 | Brauker ............... A61B 5/0031 | |
| | | | 702/19 |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Nunn et al. | |
| 7,890,295 B2 | 2/2011 | Shin et al. | |
| 7,892,206 B2 | 2/2011 | Moberg et al. | |

(56) References Cited

U.S. PATENT DOCUMENTS

| | | |
|---|---|---|
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,233,959 B2 * | 7/2012 | Kamath ............ A61B 5/14532 600/309 |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,401,606 B2 | 3/2013 | Mannheimer |
| 8,401,607 B2 | 3/2013 | Mannheimer |
| 8,657,747 B2 * | 2/2014 | Kamath ............ A61B 5/14532 600/345 |
| 8,672,845 B2 * | 3/2014 | Kamath ............ A61B 5/14532 600/345 |
| 8,961,416 B2 * | 2/2015 | Siddiqui ............ A61B 5/14532 600/365 |
| 9,135,402 B2 * | 9/2015 | Mensinger ............ A61B 5/0031 |
| 9,149,233 B2 * | 10/2015 | Kamath ............ A61B 5/0031 |
| 9,149,234 B2 * | 10/2015 | Kamath ............ A61B 5/0031 |
| 9,339,238 B2 * | 5/2016 | Shariati ............ A61B 5/0031 |
| 2001/0011224 A1 | 8/2001 | Brown |
| 2002/0026111 A1 * | 2/2002 | Ackerman ......... A61B 5/14532 600/347 |
| 2003/0050546 A1 * | 3/2003 | Desai ............ A61B 5/14532 600/347 |
| 2003/0100040 A1 | 5/2003 | Bonnecaze et al. |
| 2003/0125612 A1 | 7/2003 | Fox et al. |
| 2003/0187336 A1 | 10/2003 | Odagiri et al. |
| 2003/0208113 A1 | 11/2003 | Mault et al. |
| 2003/0208114 A1 * | 11/2003 | Ackerman ......... A61B 5/14532 600/347 |
| 2003/0211617 A1 | 11/2003 | Jones |
| 2005/0038332 A1 * | 2/2005 | Saidara ............ A61B 5/0002 600/347 |
| 2005/0049473 A1 * | 3/2005 | Desai ............ A61B 5/14532 600/347 |
| 2007/0016381 A1 * | 1/2007 | Kamath ............ A61B 5/14532 702/19 |
| 2007/0066873 A1 * | 3/2007 | Kamath ............ A61B 5/14532 600/300 |
| 2007/0123819 A1 | 5/2007 | Mernoe et al. |
| 2007/0232880 A1 * | 10/2007 | Siddiqui ............ A61B 5/14532 600/368 |
| 2008/0228055 A1 * | 9/2008 | Sher ................ A61B 5/14532 600/365 |
| 2008/0255438 A1 * | 10/2008 | Saidara ............ A61B 5/14532 600/365 |
| 2009/0113295 A1 * | 4/2009 | Halpern ............ A61B 5/14532 715/273 |
| 2009/0192745 A1 * | 7/2009 | Kamath ............ A61B 5/0031 702/85 |
| 2009/0192751 A1 * | 7/2009 | Kamath ............ A61B 5/14532 702/104 |
| 2010/0137699 A1 * | 6/2010 | Sher ................ A61B 5/14532 600/365 |
| 2010/0160861 A1 | 6/2010 | Causey, III et al. |
| 2012/0001920 A1 * | 1/2012 | Halpern ............ A61B 5/14532 345/440.2 |
| 2012/0245448 A1 * | 9/2012 | Shariati ............ A61B 5/7475 600/365 |
| 2012/0259191 A1 * | 10/2012 | Shariati ............ A61B 5/7475 600/365 |
| 2014/0184422 A1 * | 7/2014 | Mensinger ............ A61B 5/0004 340/870.02 |
| 2014/0184423 A1 * | 7/2014 | Mensinger ............ A61B 5/0004 340/870.09 |
| 2014/0187889 A1 * | 7/2014 | Cohen ................ A61B 5/14532 600/365 |
| 2014/0187890 A1 * | 7/2014 | Mensinger ............ A61B 5/0004 600/365 |
| 2014/0188398 A1 * | 7/2014 | Cohen ................ A61B 5/14532 702/19 |

FOREIGN PATENT DOCUMENTS

| | | |
|---|---|---|
| EP | 1102194 A2 | 5/2001 |
| EP | 1127544 B1 | 8/2001 |
| EP | 1102194 A3 | 2/2003 |
| JP | 2002-541883 A | 12/2002 |
| WO | 9625088 A1 | 8/1996 |
| WO | 9635370 A1 | 11/1996 |
| WO | 9856078 A1 | 12/1998 |
| WO | 9856293 A1 | 12/1998 |
| WO | 0018449 A2 | 4/2000 |
| WO | 0018449 A3 | 4/2000 |
| WO | 0019887 A1 | 4/2000 |
| WO | 0049941 A1 | 8/2000 |
| WO | 0244865 A2 | 6/2002 |
| WO | 0244865 A3 | 6/2002 |
| WO | 2004008956 A2 | 1/2004 |
| WO | 2004008956 A3 | 1/2004 |
| WO | 2004009161 A1 | 1/2004 |
| WO | 2005065538 A2 | 7/2005 |
| WO | 2005065538 A3 | 7/2005 |

* cited by examiner

SYSTEM FOR MONITORING PHYSIOLOGICAL CHARACTERISTICS

BACKGROUND OF THE INVENTION

1. Field of the Invention

This invention relates generally to medical monitoring systems. More specifically, this invention relates to methods and systems for monitoring physiological characteristics in individuals including those associated with physiological conditions (e.g. monitoring blood glucose levels in diabetics).

2. Description of the Related Art

A variety of electrochemical sensors have been developed for detecting and/or quantifying specific agents or compositions in a patient's blood. Notably, glucose sensors have been developed for use in obtaining an indication of blood glucose levels in a diabetic patient. Such readings are useful in monitoring and/or adjusting a treatment program which typically includes the regular administration of insulin to the patient. Periodic blood glucose readings significantly improve medical therapies using semi-automated medication infusion devices. Some exemplary external infusion devices are described in U.S. Pat. Nos. 4,562,751, 4,678,408 and 4,685,903, while some examples of automated implantable medication infusion devices are described in U.S. Pat. No. 4,573,994, all of which are herein incorporated by reference.

Electrochemical sensors can be used to obtain periodic measurements over an extended period of time. Such sensors can include a plurality of exposed electrodes at one end for subcutaneous placement in contact with a user's interstitial fluid, blood, or the like. A corresponding plurality of conductive contacts can be exposed at another end for convenient external electrical connection with a suitable monitoring device through a wire or cable. Exemplary sensors are described in U.S. Pat. No. 5,299,571, U.S. Pat. Nos. 5,390,671; 5,391,250; 5,482,473; and 5,586,553, which are all incorporated by reference herein.

Conventional glucose monitoring systems are somewhat limited in features that they provide to facilitate the monitoring of blood glucose levels. Typically, a glucose monitor will take readings as directed by the user and might provide a warning if a reading is deemed at an unsafe level (e.g., a hyper- or hypoglycemic condition). However, by the time the warning occurs, the user may already be experiencing negative symptoms. Furthermore, it may be unacceptable to address this by simply reducing (or raising) the value which triggers an indicator (e.g. an display, an alarm or the like) of an unsafe condition, because this may prompt a user to take "remedial" action (such as administering an additional bolus) when no unsafe condition would have actually materialized. Such an approach merely increases the occurrence of false positive alarms. As a consequence, the unnecessary "remedial" action can actually provoke an unsafe condition. As described above, although existing glucose monitors adequately detect blood glucose levels upon entering the hyperglycemic range, they do not anticipate these conditions.

As is known in the art, a glucose crash occurs when blood glucose levels of an individual are in a state of rapid decline and its symptoms are similar to those associated with hypoglycemia. The symptoms are caused by the dynamics of a declining glucose level and not by an absolute glucose level. Specific symptoms can include a feeling of light headedness, sweating, tremors, nervousness and/or disorientation. Disorientation is a particular risk to the patient. If the patient becomes disoriented while operating machinery, the patient could harm himself or others. A glucose crash can be caused by any of the following events: excess insulin administration; an unexpected increase in insulin sensitivity; a fall of free fatty acids in the blood; heavy exercise; or mental or physical stress. As previously mentioned, ordinary glucose monitors provide only for detection of hypoglycemic and hyperglycemic levels.

Impaired fasting glucose (IFG) is another condition which is not predicted by conventional glucose monitors. The American Diabetes Association (ADA) identifies IFG as an undesirable glucose condition, defined as a 126 mg/dL or higher blood glucose level at wakeup. Repeated IFG events can contribute to diabetic morbidity. One cause of IFG is an inadequate nocturnal insulin basal infusion rate. Although a patient can deal with the IFG after waking by administering an insulin bolus, it is preferable for the patient to avoid IFG incidents entirely.

Typical monitors provide only a single alarm to call attention to the user. This can be problematical in contexts of varying physiological states because a user is not made aware of the specific condition and/or the appropriate degree of urgency. In existing alarm systems, until the user investigates, there is no indication of the reason for the alarm or the severity of the situation.

Conventional monitors are designed to alert the user of unsafe conditions, however, many other factors and situations are also important to the user in managing treatment. For example, events such as meals or exercise, as well as entering calibration values are not tied to reminders issued by conventional monitors. In addition, simple alarm systems alarms can provide duplicative warnings which can frustrate users and become ignored if they are excessive.

SUMMARY OF THE INVENTION

The invention as embodied and disclosed herein pertains to apparatuses and methods for monitoring physiological characteristics such as blood glucose levels. Embodiments of the invention include dynamic monitoring functions that can perform predictive analyses to anticipate harmful conditions, such as hyperglycemic (or hyperglycemic) incidents, before they occur. These dynamic functions can be used to monitor normal physiological functions, as well as in a variety of other contexts including the optimization of athletic performance. Other embodiments of the invention include advanced alarm and reminder functions, as well as advanced data presentation tools. Embodiments of the invention disclosed herein facilitate the convenient and efficient management of diseases such as diabetes.

One embodiment of the invention includes a method of monitoring a physiological characteristic of a user using a device including an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In a preferred embodiment, the physiological characteristic value is a measure of the concentration of blood glucose in the user. In another embodiment, the process of analyzing the received signal and determining a dynamic behavior includes repeatedly measuring the physiological characteristic value to obtain a series of physiological characteristic values to determine how the physiological characteristic is changing over time.

In some embodiments of the invention, each of the series of physiological characteristic values includes a smoothing filtered group of repeated physiological characteristic value readings. In such embodiments, a slope of a line fit to the series of physiological characteristic values can be calculated if a most recent of the series of physiological characteristic values is within a qualifying range. In some embodiments of the invention, the physiological characteristic value readings may be decreasing and the slope is negative. Typically, the indicator can also include a warning alarm that is responsive to the dynamic behavior profile of the physiological characteristic value. The warning alarm can also announce an anticipated glucose crash or merely low glucose levels, depending on the operating parameters of the particular dynamic analysis, including comparison of the slope to a threshold rate (e.g., 1% to 3% per minute) and comparison of the current measured value to a qualifying range (e.g., 60 to 150 mg/dL). In typical embodiments, the series of values analyzed is taken from a defined span of time (e.g., ten to thirty minutes).

In other typical embodiments of the invention, an anticipated physiological characteristic value is determined from an extrapolated curve based upon the series of physiological characteristic values. In such embodiments the indicator can provide a warning of an anticipated morning glucose incident. In preferred embodiments, the series of values analyzed can also be taken from a defined span of time (e.g. one hour). In one embodiments, the extrapolated curve is determined from a slope of a line fit to the series of physiological characteristic values and an average of the series of physiological characteristic values. In another illustrative embodiment, the anticipated physiological characteristic value can be determined approximately three hours before an anticipated wakeup time. In addition, in certain embodiments, the indicator can be provided if the anticipated value is outside a qualifying range (e.g., approximately 60 mg/dL to 126 mg/dL).

In related embodiments of the invention, a slope of a line fit to the series of physiological characteristic values is calculated if a most recent of the series of physiological characteristic values exceeds a threshold value and the slope is positive. In such embodiments, the indicator can provide a warning of an anticipated hyperglycemic incident. In an illustrative embodiment, the series of physiological characteristic values spans a time period of approximately thirty minutes and the indicator will be provided if the slope is steeper than a threshold rate. In this context a typical threshold rate can be approximately 3% per minute and the threshold value can be approximately 180 mg/dL. In such other embodiments, the indicator can provide a warning of an anticipated hypoglycemic incident. In an illustrative embodiment, the series of physiological characteristic values spans a time period of approximately thirty minutes and the indicator will be provided if the slope is steeper than a threshold rate. In this context a typical threshold rate can be approximately 3% per minute and the threshold value can be approximately 70 mg/dL.

Another embodiment of the invention includes a physiological characteristic monitor (and corresponding methods for its use) including an input device capable of receiving a signal from a sensor and a processor capable of analyzing the received signal and providing multiple alarms, each of which can be based upon different conditions associated with the physiological characteristic value of the user. In preferred embodiments, the signal is based on a physiological characteristic value of a user. In some embodiments, the multiple alarms are distinguishable from each other and can include any one of a wide variety of signals such as audible signals, visual signals, tactile signals, displays, and/or the like.

In some embodiments of the invention, the processor determines a physiological characteristic value from the received signal and the multiple alarms are based upon that value. In such embodiments, each of the multiple alarms can then be triggered if the physiological characteristic value exceeds an associated threshold value.

In other embodiments of the invention, one of a first pair of the multiple alarms can be triggered when a narrow range of physiological characteristic values is exceeded. The first pair of the multiple alarms is typically associated with a first upper threshold value and a first lower threshold value, respectively. In further embodiments, a second pair of multiple alarms can be triggered by events a wide range of physiological characteristic values (e.g. exceeding a predetermined value). The second pair of the multiple alarms can be associated with a second upper threshold value and a second lower threshold value, respectively.

In yet another embodiment of the invention, a physiological characteristic monitoring method and device are disclosed which include an input device capable of receiving a signal from a sensor and a processor for analyzing the received signal. Typically, the signal is based on a physiological characteristic value of a user. In preferred embodiments, the processor initiates a timer based upon a condition associated with the physiological characteristic value of the user and provides a reminder to the user following expiration of the timer. In some embodiments of the invention, the reminder can include an alarm signal selected from the group consisting of an audible signal, a visual signal, a tactile signal, a display, and/or the like. Typically, the duration of the timer is preset based upon the specific initiating condition.

In preferred embodiments of the invention, conditions which trigger the one or more alarms can vary. For example, the conditions which trigger the one or more alarms can be an event marker such as meal markers, exercise markers, high blood glucose markers and low blood glucose markers. The condition(s) which trigger the one or more alarms can further be a reference value that is entered into the monitor and the reminder can indicate that a new reference value should be entered.

In other embodiments of the invention, the processor can determine a physiological characteristic value from the received signal and the triggering condition is then based upon that physiological characteristic value. For example, the triggering condition can be situations where the physiological characteristic value exceeds a predetermined threshold value.

Other embodiments of the invention include a physiological characteristic monitor including an input device capable of receiving a signal from a sensor, a processor for analyzing the received signal and determining physiological characteristic value data of the user from the received signal, a memory for storing the physiological characteristic value data of the user and a display. Typically, the signal is based on a physiological characteristic value of a user. In preferred embodiments, the display provides a retrospective display of the physiological characteristic value data. In some embodiments of the invention, the stored physiological characteristic value data includes a minimum and maximum blood glucose value and the retrospective display shows the minimum and maximum blood glucose value with a respective time and date. In other embodiments, the stored physiological characteristic value data can include a first number of excursions above an upper blood glucose value and a second number of excursions below a lower blood glucose value and the retrospective display shows the first and second number.

In other embodiments of the invention, the stored physiological characteristic value data can include a distribution of blood glucose values and the retrospective display shows a first portion of the blood glucose values above an upper blood glucose value, a second portion of the blood glucose values below a lower blood glucose value and a third portion of the blood glucose values between the upper value and the lower value. In preferred embodiments, the portions can be shown as percentages, times or numbers of readings. The display can include a total time for the physiological characteristic value data as well as the total number of readings for the physiological characteristic value data. In preferred embodiments of the invention, the first portion and the second portion can be shown as integrated values. The integrated values can be based on the sums of magnitude differences from the upper blood glucose value and the lower blood glucose value for the first and second portion, respectively. In such embodiments, the integrated values can be divided by a respective duration of sensor use.

BRIEF DESCRIPTION OF THE DRAWINGS

Referring now to the drawings in which like reference numbers represent corresponding parts throughout.

DETAILED DESCRIPTION OF THE PREFERRED EMBODIMENT

1. Overview

Embodiments of the present invention encompass methods and systems for the convenient operation of monitoring physiological characteristics ("characteristic monitoring systems"). The description provided here encompasses the architecture of the apparatus as well as its control and convenience features. The control and convenience features of the present invention can be implemented in a wide range of detailed characteristic monitoring system designs. Although embodiments of the present invention are primarily described in the context of glucose monitors used in the treatment of diabetes, the embodiments of the invention are applicable to a wide variety of patient treatment programs where a physiological characteristic is periodically monitored to use in estimating the responsive treatment. For example, embodiments of the invention can be used to determine the status and/or levels of a variety of characteristics including those associated with agents such as hormones, cholesterol, medication concentrations, pH, oxygen saturation, viral loads (e.g., HIV), or the like. As is known in the art, a sensor for the characteristic monitor can be implanted in and/or through subcutaneous, dermal, subdermal, inter-peritoneal or peritoneal tissue. Such sensors typically communicate a signal from the sensor set to the characteristic monitor.

General embodiments of the invention include a physiological characteristic monitor coupled to a sensor set. In preferred embodiments, the sensor set and monitor are for determining glucose levels in the blood and/or body fluids of the user without the use of, or necessity of, a wire or cable connection between the transmitter and the monitor.

Embodiments of the characteristic monitor system of the invention are primarily adapted for use in subcutaneous human tissue. Alternatively, embodiments of the invention can be placed in a variety of other types of physiological milieus, such as muscle, lymph, organ tissue, veins, arteries or the like, as well as being used in related environments such as animal tissue. Embodiments of the invention can provide sensor readings on an intermittent, near-continuous or continuous basis.

Embodiments of the invention include sensing and advanced predictive functions of the monitor which are designed to anticipate unsafe conditions for a user before they occur. In addition, predictive functions can be employed so that a user can obtain feedback to obtain a desired physical objective, such as maximizing athletic performance. Other functions of the monitor include multiple programmable alarms and reminders. Embodiments of the invention can include advanced display tools to facilitate easy and quick interpretation of information related to the user's condition.

2. Glucose Monitor

Figure 1:
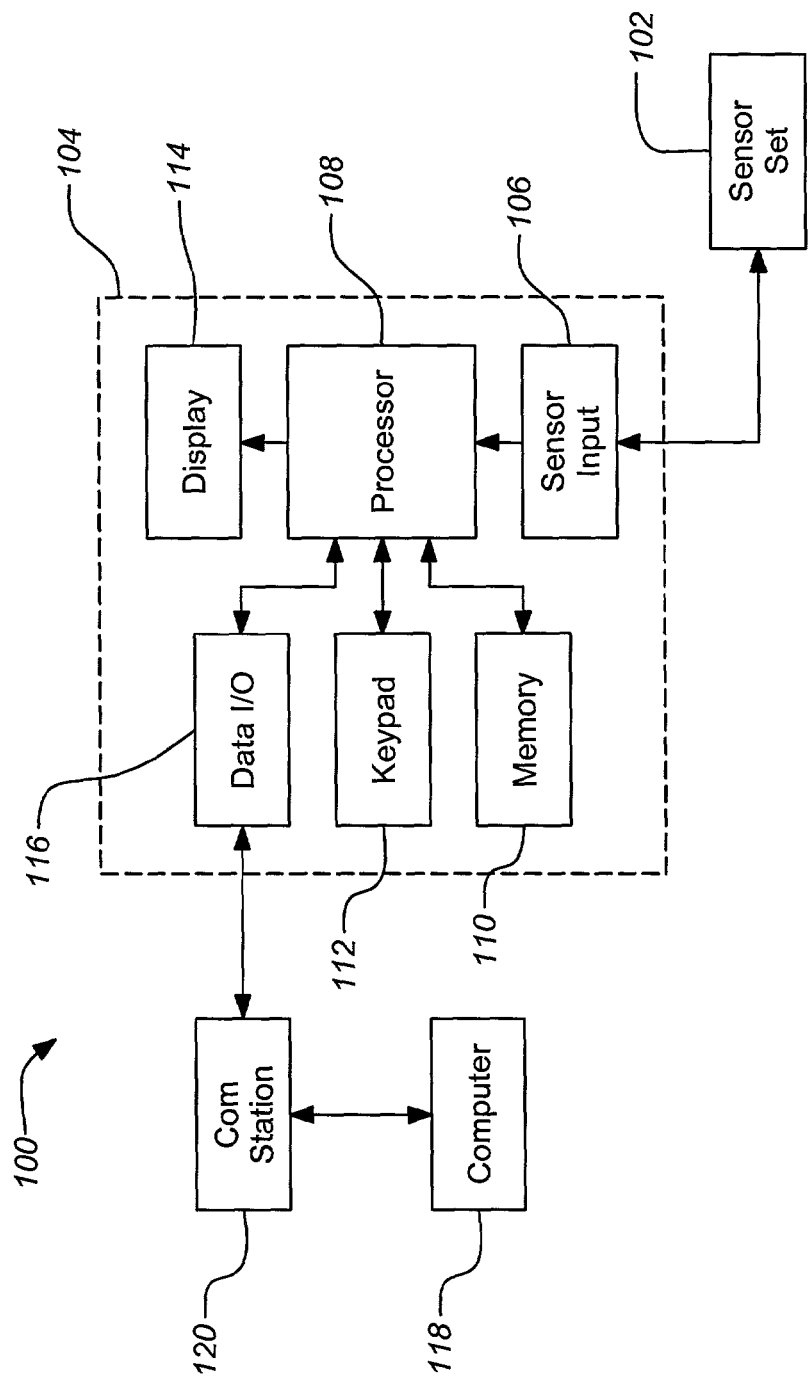
FIG. 1 is a block diagram of a characteristic monitor embodiment of the present invention.

FIG. 1 is a block diagram of a characteristic monitoring system 100 in accordance with an embodiment of the present invention. The characteristic monitoring system 100 generally includes a sensor set 102 that employs a sensor that produces a signal that corresponds to a measured characteristic of the user, such as a blood glucose level. The sensor set 102 communicates these signals to a characteristic monitor 104 that is designed to interpret these signals to produce a characteristic reading or value for the user, i.e. a measurement of the characteristic. The sensor signals enter the monitor 104 through a sensor input 106 and through the sensor input 106 the signals are conveyed to a processor 108. The processor 108 determines and manipulates the sensor readings within the monitor 104. In addition, but not limited to, the characteristic monitor 104 provides additional functions that will aid in the treatment regime to which the characteristic reading applies. For example, but not limited to, the monitor may track meals, exercise and other activities which affect the treatment of diabetes. These additional functions can be combined with or independent from the characteristic readings determined by the monitor 104.

Other components of the monitor 104 support the processor 108 in performing functions. A memory 110 is used to store data and instructions used by the processor 108. A data entry device 112 such as a keypad is used to receive direct input from the user and a display 114 such as a liquid crystal display (LCD), or the like, is used to relate information to the user. In addition, the monitor 104 includes a data port 116, such as a digital input/output (I/O) port.

The data port 116 can be used for the monitor to communicate with a computer 118. To facilitate communication, the monitor may interface with the computer 118 through a communication station 120 that can serve as a docking station for the monitor 104, for example. In some embodiments, the data port 116 within the monitor 104 can be directly connected to the computer 118. Through the communication link, data may be downloaded from the monitor, such as stored characteristic readings, settings, programs and other information related to the monitor's function. Thus, advanced analysis can be performed on a computer freeing memory 110 within the monitor 104. Data such as characteristic readings, settings and programs can also be downloaded to the monitor 104. In this way, the monitor 104 can be conveniently reprogrammed without requiring tedious manual entry by the user.

Figure 2:
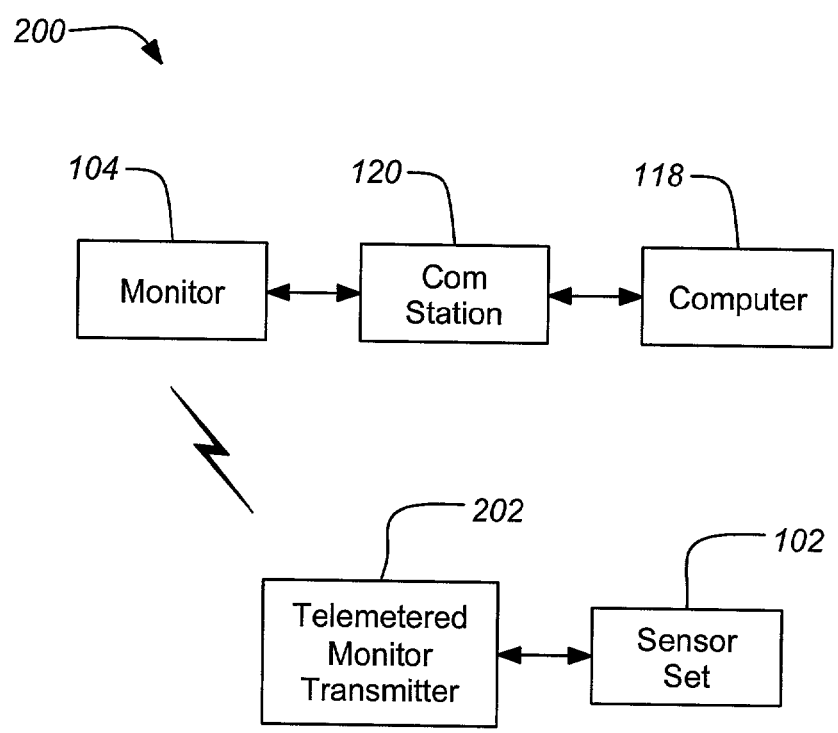
FIG. 2 is a block diagram of a telemetered characteristic monitor embodiment of the present invention.

FIG. 2 is a block diagram of a telemetered characteristic monitoring system embodiment of the invention. In this system embodiment 200, the sensor input 106 of the monitor 104 is a wireless receiver, such as a radio frequency (RF) receiver. The sensor set 102 provides a signal via wired link to a telemetered monitor transmitter 202 where the signal is interpreted and converted to an RF signal. The wireless receiver sensor input 106 of the monitor 104 converts the signal to data understandable to the monitor processor. With some advantages, the telemetered characteristic monitoring system can perform any or all the functions of the characteristic monitoring system of FIG. 1.

A characteristic monitor system 100, in accordance with a preferred embodiment of the present invention includes a sensor set 102, and characteristic monitor device 104. The sensor set 102 generally utilizes an electrode-type sensor. However, in alternative embodiments, the system can use other types of sensors, such as electrically based sensors, chemically based sensors, optically based sensors, or the like. In further alternative embodiments, the sensors can be of a type that is used on the external surface of the skin or placed below the skin layer of the user. Preferred embodiments of a surface mounted sensor utilize interstitial fluid harvested from underneath the skin. The sensor set 102 is connected to the monitor device 104 and provides a signal based upon the monitored characteristic (e.g., blood glucose). The characteristic monitor device 104 utilizes the received signal to determine the characteristic reading or value (e.g., a blood glucose level). In still other embodiments, the sensor may be placed in other parts of the body, such as, but not limited to, subcutaneous, dermal, sub-dermal, inter-peritoneal or peritoneal tissue The telemetered characteristic monitor transmitter 202 generally includes the capability to transmit data. In alternative embodiments, the telemetered characteristic monitor transmitter 202 can include a receiver, or the like, to facilitate two-way communication between the sensor set 102 and the characteristic monitor 104. In alternative embodiments, the characteristic monitor 104 can be replaced with a data receiver, storage and/or transmitting device for later processing of the transmitted data or programming of the telemetered characteristic monitor transmitter 202. In addition, a relay or repeater (not shown) can be used with a telemetered characteristic monitor transmitter 202 and a characteristic monitor 104 to increase the distance that the telemetered characteristic monitor transmitter 202 can be used with the characteristic monitor 104. For example, the relay can be used to provide information to parents of children using the telemetered characteristic monitor transmitter 202 and the sensor set 102 from a distance. The information can be used when children are in another room during sleep or doing activities in a location remote from the parents. In further embodiments, the relay can include the capability to sound an alarm. In addition, the relay can be capable of providing telemetered characteristic monitor transmitter 202 data from the sensor set 102, as well as other data, to a remotely located individual via a modem connected to the relay for display on a monitor, pager or the like. The data can also be downloaded through the communication station 120 to a remotely located computer 118 such as a PC, lap top, or the like, over communication lines, by modem or wireless connection. As disclosed herein, some embodiments of the invention can omit the communication station 120 and use a direct modem or wireless connection to the computer 118. In further embodiments, the telemetered characteristic monitor transmitter 202 transmits to an RF programmer, which acts as a relay, or shuttle, for data transmission between the sensor set 102 and a PC, laptop, communication station 118, a data processor, or the like. In further alternatives, the telemetered characteristic monitor transmitter 202 can transmit an alarm to a remotely located device, such as a communication station 118, modem or the like to summon help.

In addition, further embodiments can include the capability for simultaneous monitoring of multiple sensors and/or include a sensor for multiple measurements.

A purpose of the characteristic monitor system 100 is to provide for better treatment and control in an outpatient or a home use environment. For example, the monitor systems 100, 200 can provide indications of glucose levels, a hypoglycemia/hyperglycemia alert and outpatient diagnostics. Embodiments of the invention are also useful as an evaluation tool under a physician's supervision.

The characteristic monitor device 104 receives characteristic information, such as glucose data or the like, from the sensor set 102 and displays and logs the received glucose readings. Logged data can be downloaded from the characteristic monitor 104 to a personal computer, laptop, or the like, for detailed data analysis. In further embodiments, the characteristic monitor system 100, 200 can be used in a hospital environment, or the like. Still further embodiments of the present invention can include one or more buttons to record data and events for later analysis, correlation, or the like. Further buttons can include a sensor on/off button to conserve power and to assist in initializing the sensor set 102. The characteristic monitor 200 can also be employed with other medical devices to combine other patient data through a common data network system.

Further embodiments of the sensor set 102 can monitor the temperature of the sensor set 102, which can then be used to improve the calibration of the sensor. For example, for a glucose sensor, the enzyme reaction activity may have a known temperature coefficient. The relationship between temperature and enzyme activity can be used to adjust the sensor values to more accurately reflect the actual characteristic levels. In addition to temperature measurements, the oxygen saturation level can be determined by measuring signals from the various electrodes of the sensor set 102. Once obtained, the oxygen saturation level can be used in calibration of the sensor set 102 due to changes in the oxygen saturation levels, and its effects on the chemical reactions in the sensor set 102. For example, as the oxygen level goes lower the sensor sensitivity can be lowered. The oxygen level can be utilized in calibration of the sensor set 102 by adjusting for the changing oxygen saturation. In alternative embodiments, temperature measurements can be used in conjunction with other readings to determine the required sensor calibration.

In preferred embodiments, the sensor set 102 facilitates accurate placement of a flexible thin film electrochemical sensor of the type used for monitoring specific blood parameters representative of a user's condition. Preferably, the sensor monitors glucose levels in the body, and can be used in conjunction with automated or semi-automated medication infusion devices of the external or implantable type as described in U.S. Pat. Nos. 4,562,751; 4,678,408; 4,685,903 or 4,573,994 (which are incorporated herein by reference), to control delivery of insulin to a diabetic patient.

Embodiments of the flexible electrochemical sensor can be constructed in accordance with thin film mask techniques to include elongated thin film conductors embedded or encased between layers of a selected insulative material such as polyimide film or sheet, and membranes. The sensor electrodes at a tip end of the sensing portion are exposed through one of the insulative layers for direct contact with patient blood or other body fluids, when the sensing portion (or active portion) of the sensor is subcutaneously placed at an insertion site. The sensing portion is joined to a connection portion that terminates in conductive contact pads, or the like, which are also exposed through one of the insulative layers. In alternative embodiments, other types of implantable sensors, such as chemical based, optical based, or the like, can be used. Further description of flexible thin film sensors of this general type are be found in U.S. Pat. No. 5,391,250, entitled "METHOD OF FABRICATING THIN FILM SENSORS", which is herein incorporated by reference. The connection portion can be conveniently connected electrically to the monitor 104 or a telemetered characteristic monitor transmitter 202 by a connector block (or the like) as shown and described in U.S. Pat. No. 5,482,473, entitled "FLEX CIRCUIT CONNECTOR", which is also herein incorporated by reference. Thus, in accordance with embodiments of the present invention, subcutaneous sensor sets 102 are configured or formed to work with either a wired or a wireless characteristic monitor system 100, 200.

3. Dynamic Glucose Monitoring Functions

Embodiments of the present invention include different types of continuous glucose monitors that identify trends in blood glucose dynamics to facilitate enhanced treatment of diabetes. In general, a first illustrative monitor can be used to anticipate a glucose "crash" (or other hypoglycemic incident) before the onset of debilitating symptoms. Another illustrative monitor can be used to detect an inadequate nocturnal basal rate and alert the patient in order to avoid an impaired fasting glucose incident. Another illustrative monitor can anticipate hyperglycemic (or hypoglycemic) incidents by detecting trends toward those levels and help the patient avoid such incidents. Another illustrative monitor can assist a patient in maximizing athletic performance in endurance type activities (e.g., a marathon race) by detecting trends toward hypoglycemic levels.

The disclosed embodiments monitor the dynamics of a physiological characteristic such as blood glucose levels. These embodiments utilize this dynamic monitoring to provide functionality including the anticipation of glucose crash and alerting the patient, the detection of inadequate nocturnal basal rate, the anticipation of hyperglycemic (or hypoglycemic) incidents and maximizing athletic performance. All of these features can be implemented in software operating in the monitor's microprocessor and/or designed into an application specific integrated circuit (ASIC) or other specialized circuitry. Also, dynamic glucose monitoring functions use periodic measurements of a glucose level.

A. Monitor for Anticipating a Glucose Crash

In one embodiment of the invention, a monitor anticipates a glucose crash by monitoring trends in glucose levels. For example, the monitor can alert the patient when glucose levels are rapidly decreasing. By monitoring such trends or a rate information of measured glucose levels, the monitor can provide a much better warning system to alert the user with enough time to stabilize and reverse a dangerous physiological condition.

In some embodiments of the invention, the monitor measures glucose more frequently than typical glucose monitoring devices. For example, one embodiment of the invention measures approximately every minute, whereas other monitors measure a lower rate (e.g., but not limited to, once per 5 minutes). Frequent measurements are taken because of the short time intervals which are evaluated. Alternative embodiments may utilize more frequent measurements, such as, but not limited to, 10 seconds, 1 second, or the like.

In an illustrative embodiment, the monitor periodically measures glucose, analyzes the present trend, determines whether a glucose crash incident is probable and appropriately alerts the patient. At some frequent interval (e.g., but not limited to, once per minute), the device measures the glucose level, applies a smoothing filter to the result, and records the filtered value. The smoothing filter may take a weighted sum of past sensor values (so called finite impulse response-FIR—filter), a weighted sum of past sensor values and past filtered values (so called infinite impulse response—IIR—filters), may use simple clipping algorithms (e.g. limit the percent change in filtered output), or employ models to predict the output (e.g. Weiner and Kalman filter designs). For example, if the most recent (filtered) value is in the "qualifying range", the monitor can calculate the slope of a line fit to the most recent values (most likely, but not limited to, using a Saritzky gulag filter) and determine if the slope is steeper than a selected threshold rate (e.g., but not limited to, 3% or declining at more than 30 mg/dL in ten minutes). If the slope equals or exceeds the threshold rate, a glucose crash incident is likely and the monitor alerts the patient accordingly.

Those skilled in the art will understand that in some embodiments the qualifying range can be a closed range (e.g., but not limited to, between 100 and 150 mg/dL) and in other embodiments the qualifying range can be an open range (e.g., but not limited to, greater than 100 mg/dL). By first identifying whether a most recent value is within the qualifying range, further calculation of the dynamic behavior of the physiologic characteristic can be avoided. Thus, the determination of a glucose crash can be unconcerned with rate magnitudes occurring when the current characteristic value is outside of the range, (of course, other alarms, which merely monitor the current characteristic value, can be triggered when the reading is too high or too low). However, in alternate embodiments, the slope can be calculated and compared to the threshold rate with every new value. In further embodiments, multiple qualifying ranges and threshold rates can be applied to evaluate the glucose dynamics and determine triggering a glucose crash warning.

In one preferred embodiment, the monitor determines that a glucose crash is likely if three criteria are met. The criteria are as follows. The first, $dG/dT$ (the rate of glucose level change) is negative, can be considered for example in situations where blood glucose levels are dropping (e.g., but not limited to, when a value pertaining to the rate of glucose change is negative). The second, $IdG/dTI$ exceeds a threshold rate, can be considered in contexts, for example where a specified blood glucose change rate is exceeded for a specified sustained period (e.g., but not limited to, greater than 3% per minute for 10 minutes). The third, G, the glucose level, can be considered for example, when this value begins dropping starting within a specified range, (e.g., but not limited to, 100-150 mg/dL).

In some embodiments, these criteria can be parameterized to allow the user to customize the values. The qualifying range, threshold rate and period can be general values, applied to all users, or determined from factors specific to the individual user. For example, the monitor can include a feature to adjust the qualifying glucose level range, the maximum rate of glucose change, or in some embodiments, the sustained time period length. In addition, in some embodiments, any or all of the dynamic glucose monitoring functions can enabled or disabled, selectively or together.

The following control program pseudo code provides an example of a programming routine performed by the processor of the monitor to implement an embodiment of the invention.

```
REPEAT every minute)
{
    Measure glucose level g_i
    Filter g_i and store the filtered value g '_i
    IF(g '_i is in range 100 - 150 mg/dL)
        THEN
            Fit a line to the most recent 10 filtered (or,
alternatively, unfiltered) values
            IF (dG/dT for that line < ( - 3% per minute )
                THEN
                    Alert the patient and record in history
                ENDIF
        ENDIF
}
END REPEAT
```

Figure 3A:
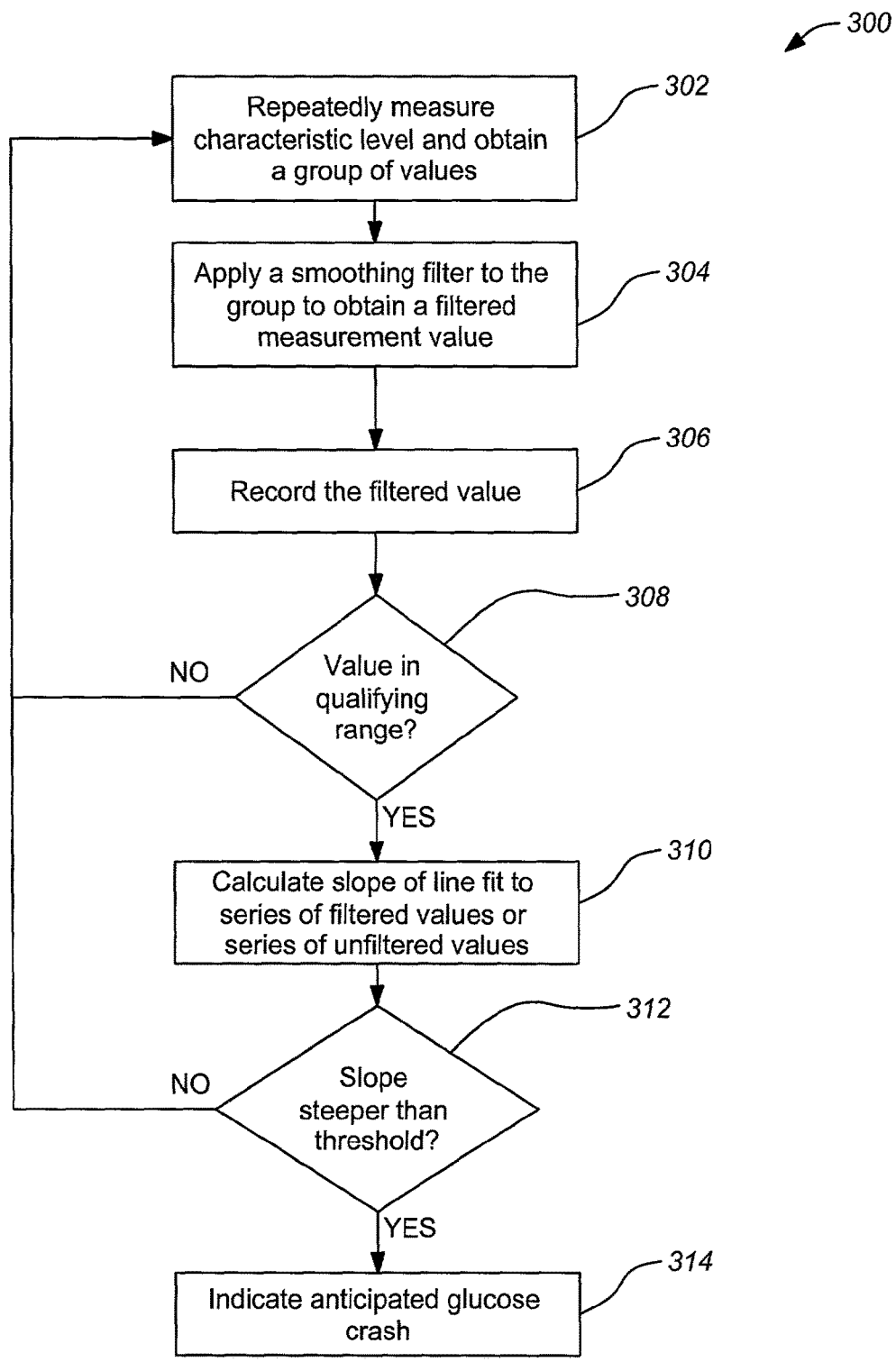
FIG. 3A is a flowchart of a method for anticipating a glucose crash.

FIG. 3A is a flowchart of a method for anticipating a glucose crash 300. At block 302, a characteristic level is repeatedly measured to obtain a group of characteristic level values. Following this at block 304, a smoothing filter can be applied to the group of characteristic level values to produce a filtered measurement value. The filtered measurement value is recorded at block 306. At block 308 it is determined if the recorded value falls within a qualifying range (e.g., but not limited to, between 100 to 150 mgldL). If not, the process returns to block 302. If the recorded measurement is within the range, a slope of a line fit to a recent series of recorded filtered values is calculated at block 310. The calculated slope is compared to a threshold rate (e.g., but not limited to, -3% per minute) at block 312. If the calculated slope is not steeper than the threshold rate the process returns to block 302. If the slope exceeds the threshold rate, an anticipated glucose crash is indicated at block 314. Alternative embodiments may utilize similar logic for when the glucose level is already outside of the range and continues to drop. In addition in an alternative preferred embodiment of the invention, one can utilize a raw data measurement (e.g. a group of characteristic level values) to determine a derivative as an alternative to using a filtered measurement value to determine a derivative.

B. Monitor for Detecting an Inadequate Nocturnal Basal Rate

In another embodiment of the invention, the characteristic monitor can be used to detect an inadequate nocturnal basal rate. This embodiment generally applies to diabetic patients using an insulin infusion device that continually administers insulin at a patient controlled basal rate. The monitor detects an inadequate basal rate (i.e., but not limited to, "low basal rate" or a "high basal rate"), by monitoring trends in glucose levels. The monitor then alerts a patient in the early morning, when glucose levels are high and relatively steady, low and relatively stable or changing rapidly. This gives the patient time to adjust the basal rate of the infusion device upward or downward to and avoid an impaired fasting glucose incident.

The monitor operates to track the characteristic level rate. For example, every 5 minutes the monitor measures and records the glucose level. Once a day (e.g., but not limited to, 3 hours before to the anticipated wakeup time), the monitor calculates the average blood glucose and the rate of blood glucose change for the previous hour. The monitor can then determine a prediction of the "morning glucose" level at wake up based upon the calculated average blood glucose and the rate of blood glucose change. In one embodiment the "morning glucose" is predicted assuming that the rate of change remains constant, however in other embodiments nonlinear characteristic curves and functions can be applied in making the prediction. If the anticipated "morning glucose" level is greater than a high threshold value (e.g., but not limited to, 126 mg/dL), or less than a low threshold value (e.g., but not limited to, 60 mg/dL), an alarm is sounded. This will allow time for the infusion device basal rate to be adjusted appropriately. In alternative embodiments, different times before anticipated wakeup, different high threshold values, or different low threshold values, may be used.

In some embodiments, the triggering criteria can also be parameterized to allow the user to customize the values. In some embodiments, the user is allowed to set the values for the controlling parameters. For example, the user can set the qualifying low and high glucose levels as well as the anticipated waking time. For each of the settings a default value can be used in the absence of a user setting. For example, a default low glucose level of 60 mg/dL, a default high glucose level of 126 mg/dL and an anticipated waking time of 7:00 AM can be used. In addition, the entire function can be enabled and disabled.

Figure 3B:
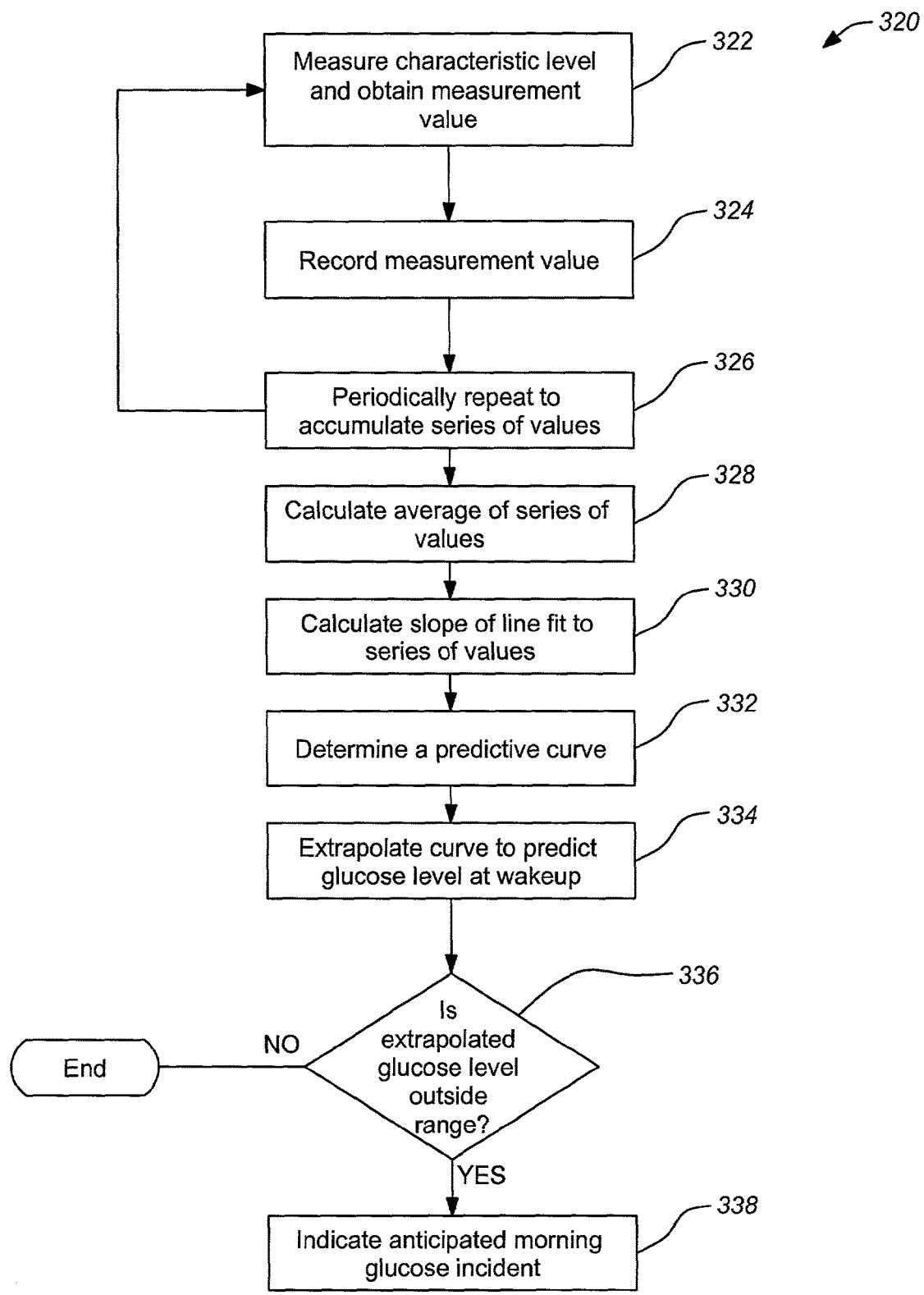
FIG. 3B is a flowchart of a method for detecting an inadequate nocturnal basal rate.

FIG. 3B is a flowchart of a method for detecting an inadequate nocturnal basal rate 320. At block 322, the method begins by measuring a characteristic level to obtain a measurement value. The value is recorded at block 324. Measuring and recording is repeated periodically to obtain a series of values at block 326. At block 328, the average of the series of values is calculated. At block 330, a slope of a line fit to the series of values is calculated. The calculated slope and average of the series of values are then used to determine a predictive curve at block 332. At block 334, the curve is extrapolated to predict a glucose level at wakeup. Those skilled in the art understand that such calculations are not limited to slope y=nix+b, and that, in this context, one can use alternative filtered arrangements as are known in the art. The extrapolation is performed some time before wakeup (e.g., but not limited to, 3 hours prior) to provide enough time to correct any impending negative condition. The predicted glucose level is compared to an acceptable range at block 336. If the predicted glucose value falls within the range, the process ends. If the predicted glucose value falls outside the range, a morning glucose incident is reported at block 338.

C. Monitor for Anticipating Hyperglycemic Incidents

In another embodiment of the invention, a glucose monitor anticipates a hyperglycemic (or hypoglycemic) incident by monitoring trends in glucose levels. The monitor alerts the patient when a "relatively steady increase" (or decrease)

in glucose levels occurs. The monitor periodically measures glucose, analyzes the present trend, determines whether a hyperglycemic (or hypoglycemic) incident is probable and appropriately alerts the patient.

In one embodiment, the device measures glucose values at a specific time interval (e.g. once every minute), and then, e.g. at 5 minute intervals, applies a smoothing filter to this group of values and records the filtered value. If the most recent (filtered) value exceeds a threshold value (e.g., but not limited to, 180 mg/dL), the monitor calculates the slope of a line fit to a recent series of recorded values (for example, but not limited to, six values). If the slope is greater than a threshold rate (e.g., but not limited to, 3% per minute), a hyperglycemic incident is likely and the monitor alerts the patient. For hypoglycemic incidents, values and thresholds corresponding to low glucose levels would be used.

The threshold value is applied in a similar manner to the "qualifying range" applied in determining a glucose crash previously discussed. The threshold value effectively operates as an open range (e.g., but not limited to, greater than 180 mg/dL). In other embodiments, the threshold value can be a closed range. Therefore, determining a hyperglycemic incident can be unconcerned with values below the threshold value (as determining a hypoglycemic incident can be unconcerned with values above a threshold value). In one embodiment, a slope calculation can be avoided if the current reading is outside the range. However, in alternate embodiments, the slope can be calculated and compared to the threshold rate with every new reading. In further embodiments, multiple qualifying ranges and threshold rates can be applied to evaluate the glucose dynamics and determine triggering a hyperglycemic (or hypoglycemic) incident warning.

Here again, in some embodiments the criteria can be parameterized to allow the user to customize the controlling values for anticipating hyperglycemic (or hypoglycemic) incidents. For example, some embodiments can allow the user to set the glucose threshold level and/or the threshold rate. Embodiments of the invention can also use default parameters if no user settings are provided (e.g., but not limited to, a threshold level of 180 mg/dL and a maximal rate of 3% per minute). Embodiments of the invention can also enable and disable this function.

Figure 3C:
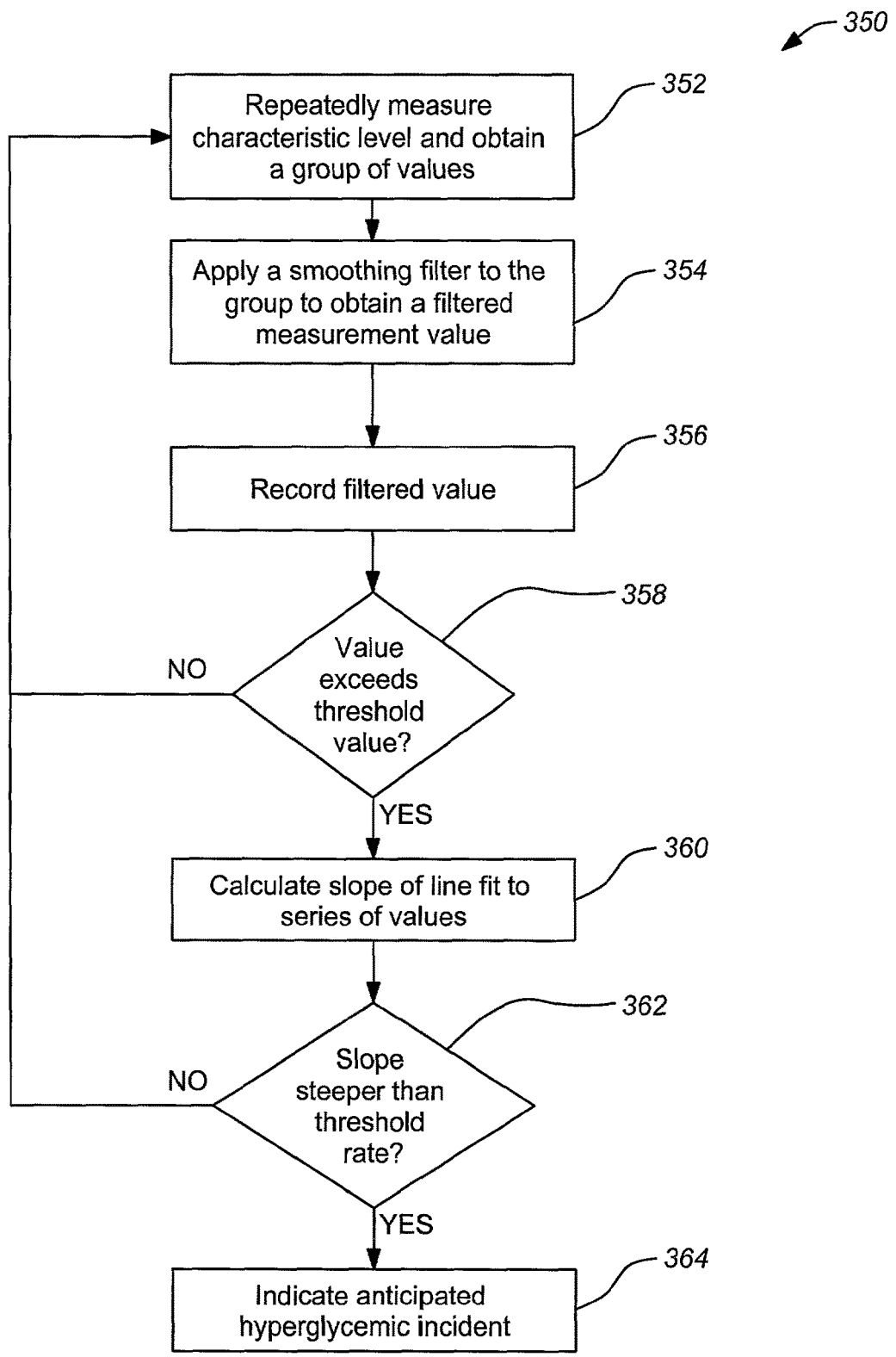
FIG. 3C is a flowchart of a method for anticipating a hyperglycemic incident.

FIG. 3C is a flowchart of a method for anticipating a hyperglycemic incident 350. The method begins at block 352 by repeatedly measuring a characteristic level to obtain a group of values. At block 354, a smoothing filter is applied to the group of values to obtain a filtered measurement value. The filtered value is recorded at block 356. The recorded value is compared to a threshold value at block 358. If the recorded value does not exceed the threshold value (e.g., but not limited to, 180 mg/dL), the process returns to block 352. If the recorded value does exceed the threshold value, a slope of a line fit to a recent series of values is calculated at block 354. The calculated slope is compared to a threshold rate (e.g., but not limited to, +3% per minute) at block 362. If the slope is not steeper than the threshold rate, the process returns to block 352. If the slope is steeper than the threshold rate, an anticipated hyperglycemic incident is reported at block 364. For hypoglycemic incidents, corresponding steps for low glucose levels would be used. As noted previously, estimates of dG/dt may be calculated by a variety of methods known in the art including the slope (and that such calculations are not limited to, for example, determinations based on y=mx+b).

D. Monitor for Maximizing Athletic Performance

Dynamic monitoring can also be used to provide feedback based upon the engaged activity of the user. For example, the monitor can be used to maximize performance during an endurance type activity (e.g., but not limited to, a marathon race). The endurance athlete strives to burn glucose rather than fat and accordingly needs to anticipate low glucose levels and ingest carbohydrates early enough to avoid low glucose levels.

In such embodiments, the monitor anticipates low glucose levels and alerts the athlete to ingest carbohydrates. It is important to note that this embodiment is not strictly anticipating hypoglycemic incidents. Instead it is anticipating low glucose levels where it would otherwise be too late for the athlete to compensate by ingesting carbohydrates and still perform effectively and/or at full capacity.

In one embodiment, once a minute, the device measures a glucose level, applies a smoothing filter and records the filtered value at 5-minute intervals. If the most recent recorded (i.e., filtered) value is in a qualifying range (e.g., but not limited to, 60-140 mg/dL), the processor calculates the slope of a line fit to the most recent six filtered values and determines if the slope is steeper than −1% (i.e., but not limited to, 30 mg/dL in 30 minutes). If the rate of decline exceeds this threshold, a low glucose level is likely and the monitor alerts the athlete accordingly. Thus, for example, but not limited to, to trigger an alarm, the glucose level rate, dG/dT, is negative with a magnitude greater than 1% per minute for 30 minutes beginning in range 60-140 mg/dL.

Similar to the glucose crash monitor, in embodiments for maximizing athletic performance the qualifying range can be a closed range (e.g., but not limited to, between 60 and 140 mg/dL) or an open range (e.g., but not limited to, less than 140 mg/dL). By first identifying whether a most recent value is within the qualifying range, further calculation of the dynamic behavior of the physiologic characteristic is avoided. Although, other alarms which merely monitor the current characteristic value can be triggered when the reading is too high or too low. However, in alternate embodiments, the slope can be calculated and compared to the threshold rate with every new value. In further embodiments, multiple qualifying ranges and threshold rates can be applied to evaluate the glucose dynamics and determine triggering a low glucose warning.

Here too, these criteria can be parameterized to allow the user to customize the values. Typically, the monitor will allow a user to set the qualifying glucose range and/or enable and disable the function. A default qualifying range (e.g., but not limited to, 60-140 mg/dL) can be used.

Figure 3D:
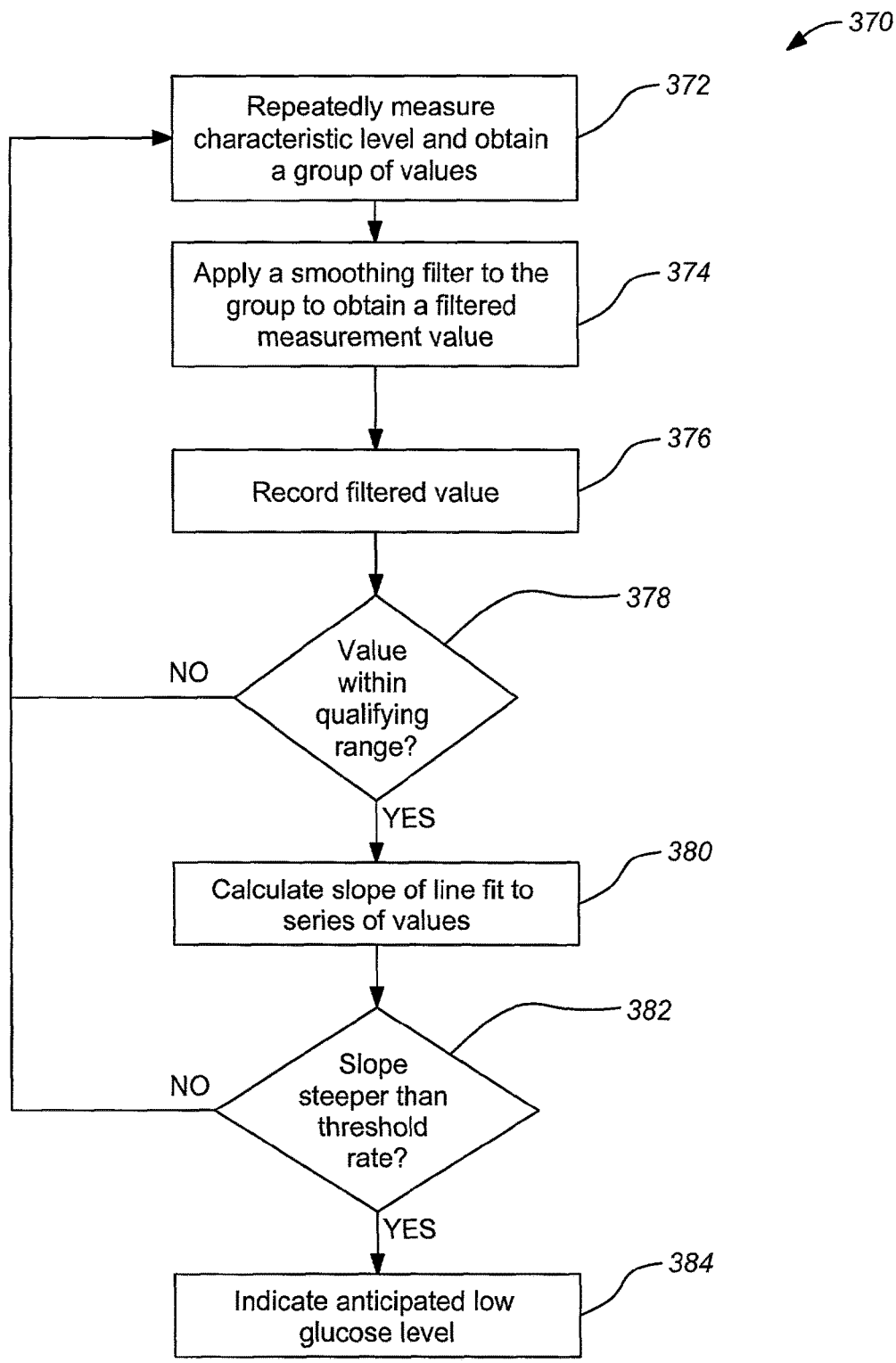
FIG. 3D is a flowchart of a method for maximizing athletic performance.

FIG. 3D is a flowchart of a method for maximizing athletic performance 370. The process begins at block 372, where a characteristic level is repeatedly measured to obtain a group of characteristic level values. Following this at block 374, a smoothing filter can be applied to the group of characteristic level values to produce a filtered measurement value. The filtered measurement value is recorded at block 376. At block 378 it is determined if the recorded value falls within a qualifying range (e.g., but not limited to, between 60 to 140 mg/dL). If not, the process returns to block 372. If the recorded measurement is within the range, a slope of a line fitted to a recent series of recorded filtered values is calculated at block 380. The calculated slope is compared to a threshold rate (e.g., but not limited to, −1% per minute) at block 382. If the calculated slope is not steeper than the threshold rate the process returns to block 372. If the slope exceeds the threshold rate, an anticipated low glucose level is indicated at block 384. As noted previously, estimates of dG/dt may be calculated by slope as well as other methods known in the art 4. Multiple Glucose Alarm Function Embodiments of the invention can also employ multiple alarms that can be independently set by the user. For example, a continuous glucose monitoring system can have multiple alarms for different glucose values. The system can allow a user to set threshold glucose values that define a "narrow" glucose range (as compared to the ordinary alarm limits). If the user's glucose level passes outside the "narrow" range, an alarm can sound. This alarm alerts the user to monitor his glucose levels more closely. The system can sound a second alarm (preferably having a sound distinguishable from the first "narrow" range alarm) in the even the user's glucose level reaches a more dangerous condition requiring immediate action. Alarm indications may be audible, tactile, vibratory, visual, combinations of alarm indications, or the like. In the case of visual alarm indications, but not limited to, green lights can be displayed for with a range; yellow for the first alarm level; and red for the second alarm level. The visual alarm indications may flash and/or also be combined with other alarm indications.

Although the above example describes a two-layer alarm system, further embodiments of the invention can incorporate multiple alarm layers. In addition, the alarms can be set in ranges or separate high and low glucose level alarms can be set. Distinctive sounds can be used for each alarm. For example, each successive high glucose level alarm can have, but is not limited to having, a higher pitch. Successive low glucose level alarms can each have, but are not limited to having, lowering pitches. Alternately, intermittent or wavering volumes that also increase in pitch according to the severity of the condition can be used. In still other embodiments, the user can select or program alarm tones and other sounds and assign them to the various alarms. Also, in some embodiments, these distinguishable alarms can also be set at different volume levels. In addition, as discussed above, the alarms are not limited to audible signals; some embodiments of the invention can also utilize visual alarms, such as flashing lights or displays or tactile alarms, such as vibrating indicators.

In still further embodiments, threshold values and associated alarms can be set according to a schedule. For example, but not limited to, particular alarms can be set to be active only during selected portions of the day.

Figure 4:
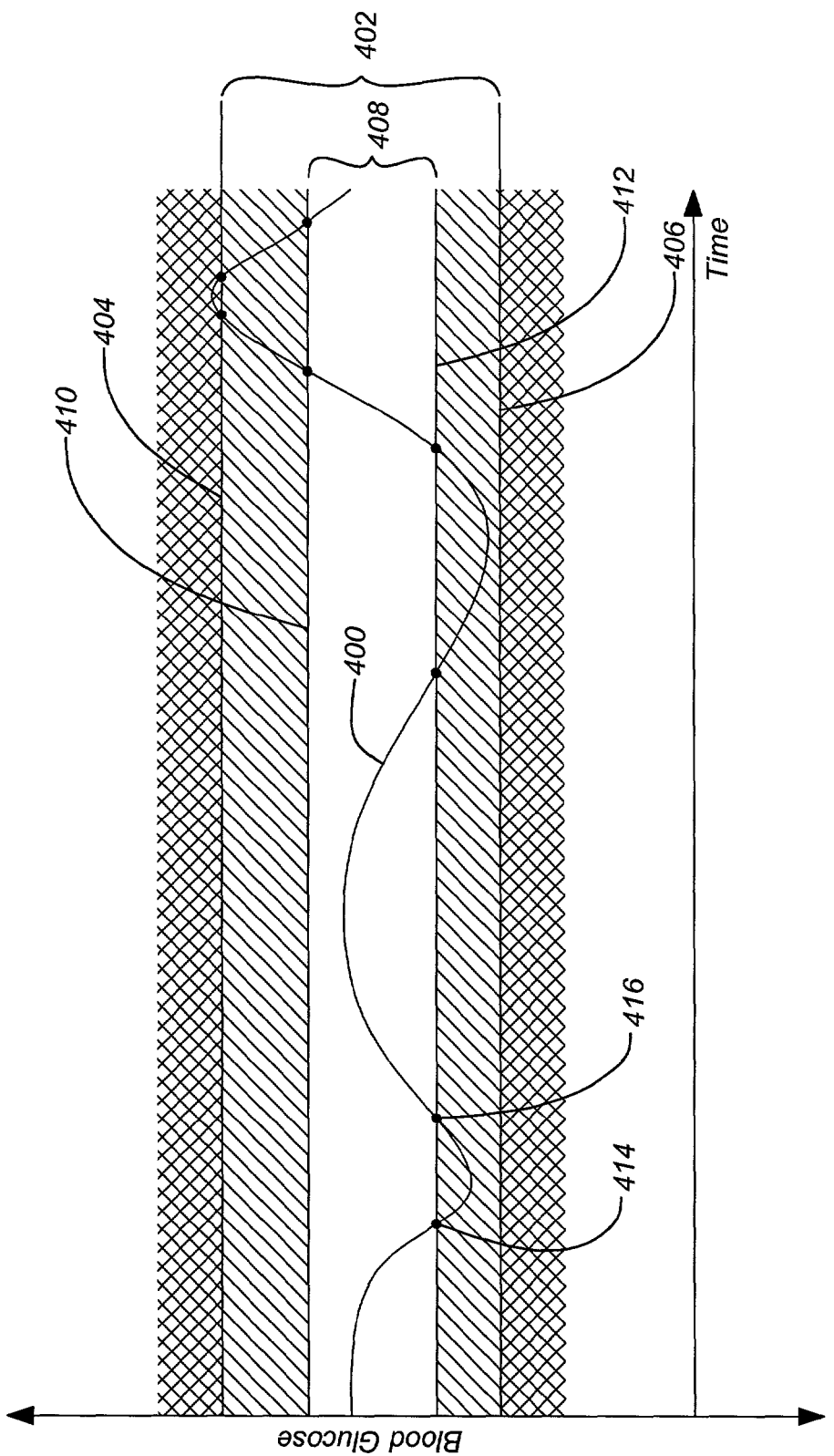
FIG. 4 illustrates a multiple alarm function of the invention.

FIG. 4 illustrates a multiple alarm function of the invention. A plot of the monitored characteristic value 400 (e.g., blood glucose) changing over time is shown. A typical wide alarm range 402 is defined by an upper threshold value 404 and a lower threshold value 406. If the monitored characteristic value 400 should exceed the defined range and cross either threshold, an alarm is initiated to indicate to the user to check his blood glucose. In one embodiment, a distinctive alarm can be associated with the alarm range 402. Thus, the same alarm is produced whether the range 402 is exceeded by passing the upper threshold value 404 or the lower threshold value 406. In other embodiments, distinctive alarms can be assigned to each threshold value 404, 406. In further embodiments of the invention, other alarm ranges can also be set. For example, a second narrower range 408 can be set with a lower upper threshold value 410 than that of the wider range 402; and a higher lower threshold value 412 than that of the wider range 402. As with the wider range 402, an alarm is initiated if the narrower range is exceeded by the monitor characteristic value 400. Here also, alarms can be the same or different for each threshold 410, 412.

The ability to set different ranges and associated alarms allows the monitor to immediately convey some information about the condition of the user even before checking the actual readings. Particularly, using the narrower range 408 and associated alarms allows the user to know of a negative trend that does not require the same urgency as an alarm triggered by the wider range 402. In effect, the user is able to set multiple alarms, each indicating a different level of urgency and/or different conditions. In some embodiments, threshold values for alarms can also be set independent from ranges.

In addition, in still further embodiments alarms or indicators can be set according to the direction in which a threshold value is crossed by the monitored characteristic value 400. For example, as the monitored characteristic value 400 crosses a lower threshold value 412 from the narrow range (e.g., but not limited to, at point 414), one type of alarm can be provided. However, when the monitored characteristic value 400 crosses a lower threshold value 412 from the wider range 402 (e.g., but not limited to, at point 416), another type of alarm can be provided. The difference in the alarms is appropriate because only the former case indicates a worsening of the user's condition. In the latter case, the transition actually indicates an improvement in the user's condition. Thus, in some embodiments of the invention, alarms will only be given when crossing a threshold indicates a worsening of the user's condition. In other embodiments, an indicator will also be given when a threshold has been crossed in an improving direction. In these cases, either the same indicator (sound, light, display or other) or different indicators can be used. In a similar manner, reminders can be set to indicate to a user various conditions (not necessarily negative) that will aid in the convenient therapy management.

5. Advanced Blood Glucose Reminder Functions

Another aspect of the invention allows the user to set reminders that will be provided by the monitor. The reminders can be alarm signals (including, but not limited to, auditory, visual, tactile, etc.) that are initiated after a timer has run to prompt the user to take action or merely inform the user of a particular status. The reminder is started (i.e. the timer is initiated), when an event occurs and/or certain conditions are met. The alarm signals can be the same or different based upon the triggering events or conditions. These reminders can be used to further assist the user in managing insulin delivery for optimum results. For example, but not limited to, reminders can be set for event markers, blood glucose values, reference values, high or low sensor measurements.

Characteristic monitors and infusion devices can use event markers that place tags in the data for events the user experiences (e.g., but not limited to, meals, exercise, and high or low blood glucose). For example, but not limited to, when an infusion device identifies a high or low blood glucose event marker, it can start a timer that reminds the user to check blood glucose levels. This is intended to make therapy safer by encouraging more frequent checks during times that the patient may be at risk from hypoglycemia or hyperglycemia. In addition, this feature can also be applied to characteristic monitors. For example, but not limited to, a characteristic monitor that is used to show low or high blood glucose tags can have a timer set to remind a user to check their blood glucose levels at a later time.

In addition, a reminder timer can be set that is triggered if a blood glucose value is entered. For example, but not limited to, the reminder can be if the user enters a low or high blood glucose value into the monitor as a reference or calibration value.

A reminder timer can also be triggered by a user providing a reference value to the monitor. Thus, the user can be reminded to supply a new reference value after a minimum time period has elapsed. In this way calibration of the monitor is assured.

A blood glucose reminder can also be triggered by high or low measurement from the sensor. Thus, the monitor will request a blood glucose reference value during an excursion away from the normal range of values. The trigger for this reminder can be tempered by setting a minimum time between reminders to avoid pestering the user. This reminder can be used to provide more robust data for curve fitting as correlation improves with variability in the data pairs. The reminder promotes more frequent data collection during more critical periods (e.g., but not limited to, when blood glucose is too high or too low) and therefore the interpolated curve for this period is more reliably representative of the true curve.

One aspect behind the use of these reminders is that they also serve to prevent redundant and excessive alarms for the user. For example, if the timer is removed from the previously described high or low measurement reminder, the result would be a simple hypoglycemia or hyperglycemia alarm. Using a reminder, however, the message is not that the user's blood glucose is out of range. Rather, the reminder's message is to check the user's blood glucose with a meter, or the like. If a user's blood glucose is very near an alarm triggering threshold, an alarm might be triggered repeatedly as the value passes back and forth across the threshold. A reminder will set a timer, preventing duplicative warnings for a short period of time, but reminding the user to check blood glucose again when that period has expired. This can provide a better or easier path through the regulatory process. Thus, reminders are less likely to become a nuisance to the user and also prompt more useful data collection. In alternative embodiments, the alarm is triggered again, regardless of the presence of a time, if the glucose level continues to change in the direction of the trend.

Figure 5:
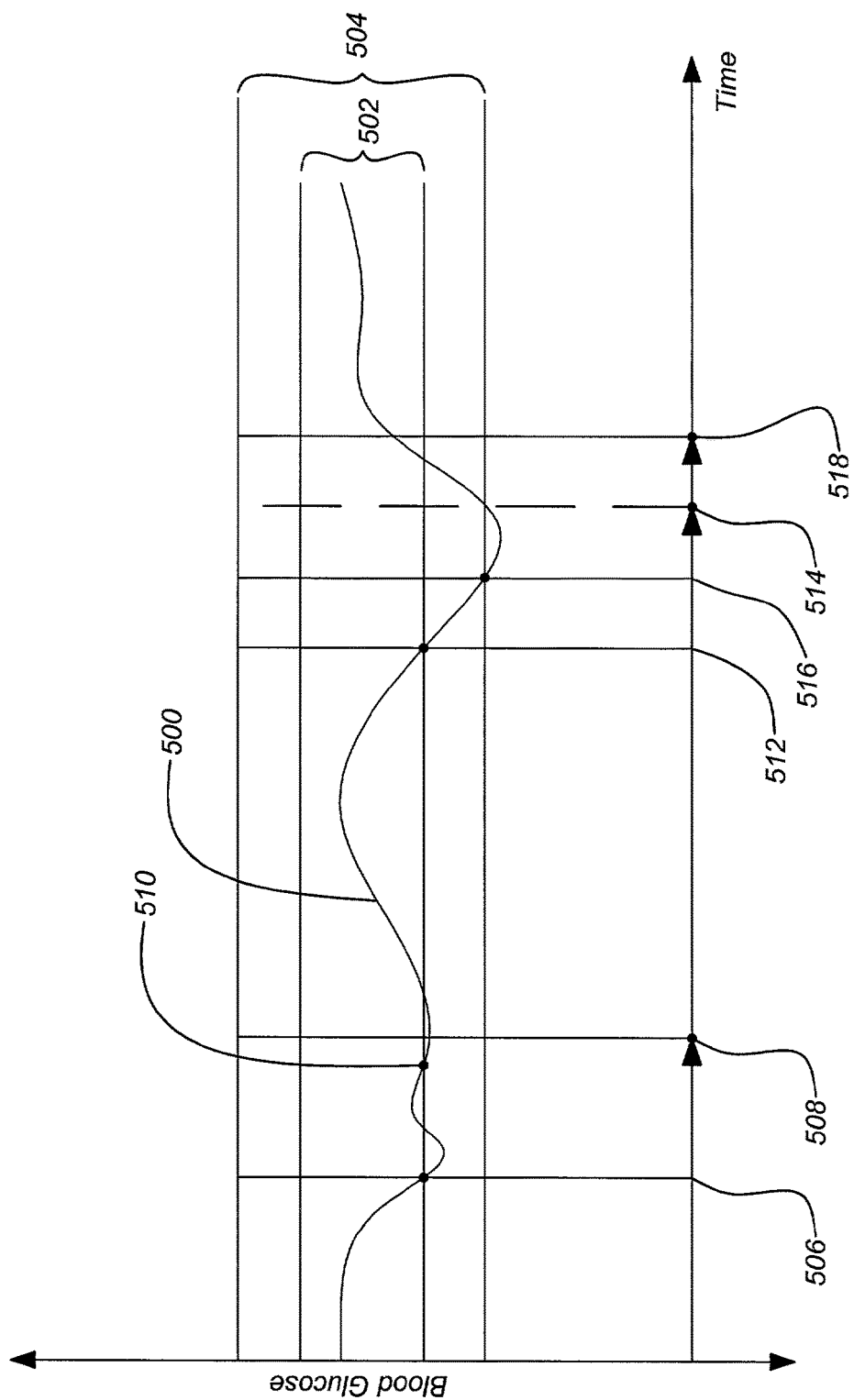
FIG. 5 illustrates a reminder function of the invention.

FIG. 5 illustrates a reminder function of the invention triggered by high or low characteristic values. A plot of a monitored characteristic value 500 (such as, but not limited to, blood glucose) is shown. One or more ranges 502, 504 define safe characteristic values (e.g., but not limited to, a first range 502 being a warning range and a second range 504 being a critical range), such as can be employed using multiple alarms as previously described. When a range is exceeded (e.g., but not limited to, at time 506), an alarm can be triggered but also a timer is started such that a reminder is also initiated after its expiration (e.g., but not limited to, at time 508). Over the timer period further occurrences of exceeding the threshold (e.g., but not limited to, at point 510) will not result in a duplicative alarm.

However, the situation can be somewhat different when the intervening triggering event is not identical to the first triggering event. For example, if a first range 502 is exceeded (e.g., but not limited to, at time 512) and a timer is started, but before a reminder can be issued (e.g., but not limited to, at time 514) a second range 504 is exceeded (e.g., but not limited to, at time 516), then the second alarm will be issued and the timer will be restarted. No reminder will be indicated at the theoretical expiration of the first timer (e.g., but not limited to, at time 514), but a reminder will be issued at the expiration of the second timer (e.g., but not limited to, at time 518). In this case, exceeding the second range overrides the first reminder because the second alarm is a different, albeit related, condition. As previously described, however, the use of reminders is not limited to monitoring high and low characteristic values. In a similar manner, reminders can be triggered by user's supplied reference values for calibration as well as event markers entered into the monitor.

6. Glucose Monitoring Information Management

Another aspect of the invention is to provide meaningful retrospective information to the patient using the sensor. In particular, a retrospective display of one or more physiological values can provide significantly useful data. As disclosed, the retrospective displays can be designed in a variety of ways to provide various useful information. For example, but not limited to, as the sleeping user receives no benefit from a real-time display, a retrospective view of data is important. While a simple listing of previous values has value, it can be time consuming to review, provides information that is difficult to visualize and comprehend and requires significant memory space within the device. Providing useful information that is easy to understand and that can be stored within a small memory space is very important. The ability to review data from the previous sleep period is particularly helpful to a user with nocturnal hypoglycemia or "dawn effect", as there is typically no witness to the real-time display. These measures can be even more important in cases where the alarm system can exhibit many false positives and/or false negatives, which might otherwise frustrate the user and lead to non-use of the monitor.

The following advanced data presentation tools can be used to conveniently and efficiently store and display useful information on a screen for a user to review while the monitor is in use. The tools provide useful information while requiring only a minimal amount memory space. These data presentation tools can also be used in any retrospective analysis package, such as software running on a computer or network designed to analyze trends and provide advise regarding a treatment regime.

The tools operate by processing that compares actual reading to high and low value limits (e.g., but not limited to, acceptable blood glucose ranges). For example, but not limited to, the limits can be the adjustable hypoglycemic and hyperglycemic alarm thresholds of a monitor. Alternately, for standardization, the tools can be applied to a fixed definition of a target blood glucose range that is independent of the hyperglycemic and hypoglycemic alarm thresholds for the particular user/monitor.

Figure 6A:
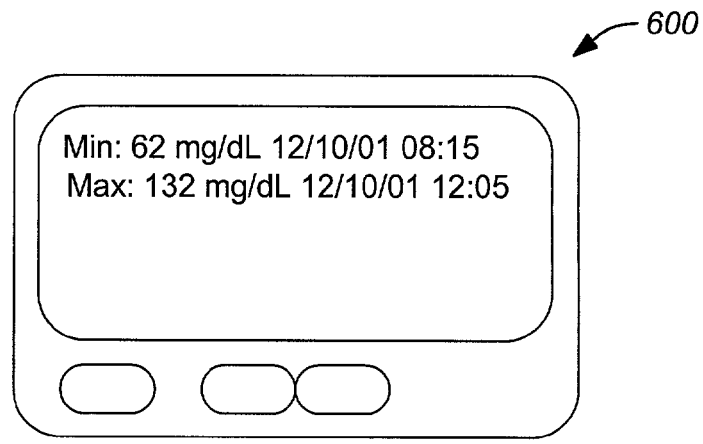
FIG. 6A illustrates minimum and maximum data presentation.
Figure 6B:
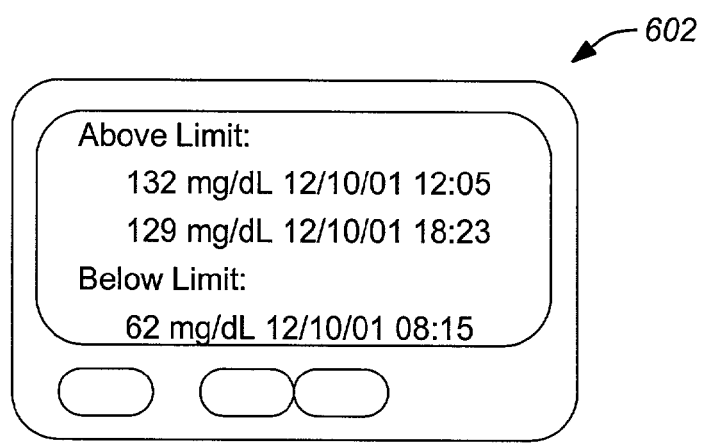
FIG. 6B illustrates excursion data presentation.

FIG. 6A illustrates one minimum and maximum data presentation. A display of the minimum and maximum values 600 of the characteristic monitor that have been measured for the user can be displayed on the monitor. The minimum value and maximum values can be conveniently displayed along with the date and time of their occurrence. Such a display 600 is useful, but becomes more useful when combined with an excursion count, a distribution of values, and/or integrated values as discussed below FIG. 6B illustrates an excursion data presentation. The number of excursions above or below the respective blood glucose limits is also very useful to have summarized for the user. An excursion display 602 provides good information, particularly when there are no alarms active on the monitor (either because the monitor is not turned on or alarms are not being employed by the user). A display 602 of the number of excursions above the hyperglycemic limit and the number of excursions below hypoglycemic limit give the user an idea of performance of a treatment program at a glance. A high number of incidents exceeding either limit indicate a need for improvements.

Figure 6C:
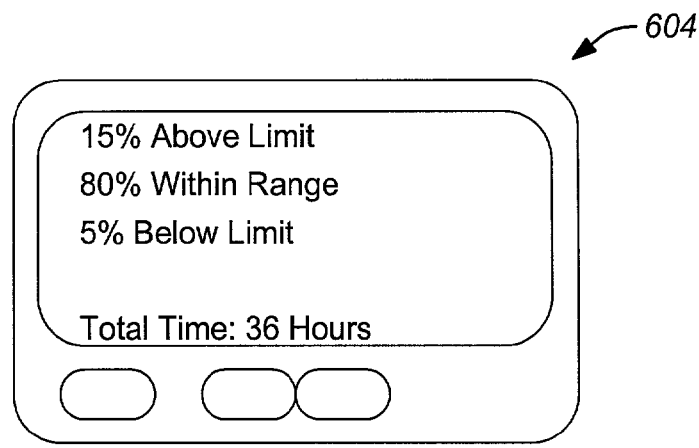
FIG. 6C illustrates characteristic value distribution data presentation.

FIG. 6C illustrates a characteristic value distribution data presentation. A simple distribution of sensor values offers a very powerful tool. In a preferred embodiment, the distribution is described in percentages that are automatically scaled with the duration of monitor use. Optionally, a monitor can include the total time of use with a percentage distribution. Awareness of a total time provides perspective for reviewing the percentage distribution. A time based distribution can also be used, but requires the total time to be included in the analysis as a reference. A distribution can also be presented based upon the total number of readings, but requires the total time is required in the analysis.

For example, but not limited to, the display can show a percentage of readings above a hyperglycemic alarm level, a percentage of readings below a hypoglycemic alarm level and a percentage of readings of readings within alarm range as shown in FIG. 6C. Optionally, the total time covered in the analysis can also be displayed. Similarly, an alternate display can show the time spent above a hyperglycemic alarm level, the time spent below a hypoglycemic alarm level and the time spent within alarm range (not shown). As mentioned, the time base display requires a known total time as part of the analysis. Finally, a display can also include the number of readings above hyperglycemic alarm level, the number of readings below a hypoglycemic alarm level and the number of readings within alarm range (not shown).

Figure 6D:
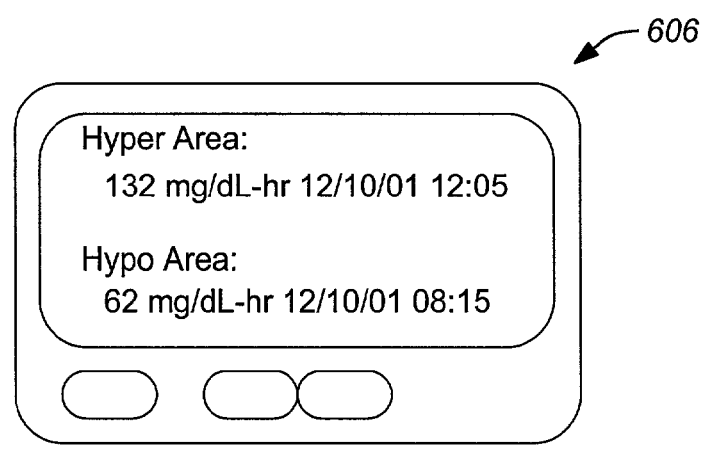
FIG. 6D illustrates integrated characteristic value data presentation.

FIG. 6D illustrates an integrated characteristic value data presentation. Performing an integration of the readings outside the alarm levels with respect to time can provide a measure of the hypoglycemic and hyperglycemic events' severity. In addition, these results can also be scaled these by a total sensor time to provide a measure that is duration independent.

For example, a "hyperglycemic area" can be calculated as the sum of the differences between the readings and the hyperglycemic alarm limit. A "hypoglycemic area" can be calculated from the sum of all the differences between the hypoglycemic alarm limit and the readings. A "hyperglycemic index" is calculated by taking the "hyperglycemic area" and dividing it by the duration of sensor use. Similarly, the "hypoglycemic index" can be calculated by taking the "hypoglycemic area" divided by the duration of sensor use.

CONCLUSION

Various alarms and/or monitoring aspects discussed above may be combined or utilized with other alarms and/or monitoring aspects. The possible embodiments and/or combinations should not be limited to the specific embodiments described above.

This concludes the description including the preferred embodiments of the present invention. The foregoing description including the preferred embodiment of the invention has been presented for the purposes of illustration and description. It is not intended to be exhaustive or to limit the invention to the precise form disclosed. Many equivalent modifications and variations are possible in light of the above teaching.

It is intended that the scope of the invention be limited not by this detailed description, but rather by the claims appended hereto. The above specification, examples and information provide a description of the manufacture and use of the apparatus and method of the invention. Since many embodiments of the invention can be made without departing from the scope of the invention, the invention resides in the claims hereinafter appended. Throughout this application, various publications are referenced. The disclosures of these publications are hereby incorporated by reference herein in their entireties.

What is claimed is:

1. A glucose monitor system, comprising:
 a sensor set to produce signals corresponding to blood glucose levels of a user; and
 a glucose monitor, including
  a processor to receive the signals from the sensor set, analyze the signals received, and provide multiple alarms, wherein
   a first upper alarm of the multiple alarms is associated with a first upper threshold value and a first lower alarm of the multiple alarms is associated with a first lower threshold value for a first range of rates of glucose level change, and
   a second upper alarm of the multiple alarms is associated with a second upper threshold value and a second lower alarm of the multiple alarms is associated with a second lower threshold value for a second range of rates of glucose level change, and
  a display to provide visual alarm indications based on the multiple alarms corresponding to the first upper threshold value, the first lower threshold value, the second upper threshold value, and the second lower threshold value, wherein the multiple alarms are distinguishable from each other.

2. The glucose monitor system of claim 1, further including a telemetered monitor transmitter coupled to the sensor set, wherein the sensor set provides the signals to the telemetered monitor transmitter and the telemetered monitor transmitter interprets and converts the signals to RF signals to be wirelessly transmitted to the glucose monitor.

3. The glucose monitor system of claim 1, wherein the glucose monitor further includes a sensor input coupled to the processor to wirelessly receive the signals from the sensor set.

4. The glucose monitor system of claim 1, wherein the visual alarm indications include at least one of a colored light, a flashing light, and a display.

5. The glucose monitor system of claim 1, wherein the display relates information to the user based on the signals received from the sensor set.

6. A glucose monitor, comprising:
 a processor to receive signals corresponding to blood glucose levels of a user from a sensor set, analyze the signals received, and provide multiple alarms, wherein
  a first upper alarm of the multiple alarms is associated with a first upper threshold value and a first lower alarm of the multiple alarms is associated with a first lower threshold value for a first range of rates of glucose level change, and
  a second upper alarm of the multiple alarms is associated with a second upper threshold value and a second lower alarm of the multiple alarms is associated with a second lower threshold value for a second range of rates of glucose level change, and
 a display to provide visual alarm indications based on the multiple alarms corresponding to the first upper threshold value, the first lower threshold value, the second upper threshold value, and the second lower threshold value, wherein the multiple alarms are distinguishable from each other.

7. The glucose monitor of claim 6, further including a sensor input coupled to the processor to wirelessly receive the signals from the sensor set.

8. The glucose monitor of claim 6, wherein the visual alarm indications include at least one of a colored light, a flashing light, and a display.

9. The glucose monitor of claim 6, further including a telemetered monitor transmitter coupled to the sensor set, wherein the sensor set provides the signals to the telemetered monitor transmitter and the telemetered monitor transmitter interprets and converts the signals to RF signals to be wirelessly transmitted.

10. The glucose monitor of claim 6, wherein the display relates information to the user based on the signals received from the sensor set.

11. A method of providing alarms for a glucose monitor, comprising:
   receiving signals corresponding to blood glucose levels of a user from a sensor set;
   analyzing the signals received from the sensor set;
   providing visual alarm indications corresponding to multiple alarms, wherein
   a first upper alarm of the multiple alarms is associated with a first upper threshold value and a first lower alarm of the multiple alarms is associated with a first lower threshold value for a first range of rates of glucose level change,
   a second upper alarm of the multiple alarms is associated with a second upper threshold value and a second lower alarm of the multiple alarms is associated with a second lower threshold value for a second range of rates of glucose level change, and
   the multiple alarms corresponding to the first upper threshold value, the first lower threshold value, the second upper threshold value, and the second lower threshold value are distinguishable from each other.

12. The method of claim 11, further including producing the signals corresponding to the blood glucose levels of the user from the sensor set.

13. The method of claim 11, wherein the visual alarm indications include at least one of a colored light, a flashing light, and a display.

* * * * *